(12) United States Patent
Daniel

(10) Patent No.: US 9,554,937 B2
(45) Date of Patent: Jan. 31, 2017

(54) PENILE PROSTHETIC PUMP HAVING AN INLET VALVE WITH A LOCKOUT FLANGE

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 276 days.

(21) Appl. No.: 14/304,984

(22) Filed: Jun. 16, 2014

(65) Prior Publication Data

US 2015/0359655 A1  Dec. 17, 2015

(51) Int. Cl.
A61F 2/26 (2006.01)
A61F 5/41 (2006.01)
A61M 39/22 (2006.01)

(52) U.S. Cl.
CPC . *A61F 5/41* (2013.01); *A61F 2/26* (2013.01); *A61F 2005/415* (2013.01); *A61M 39/227* (2013.01)

(58) Field of Classification Search
CPC ..... A61F 2/26; A61B 17/04; A61B 17/06066; A61B 17/3468; A61B 2017/06052
USPC .......................................... 600/38–41, 29–32
See application file for complete search history.

(56) References Cited

U.S. PATENT DOCUMENTS

| | | |
|---|---|---|
| 3,533,719 A | 10/1970 | Cobarg et al. |
| 3,734,258 A | 5/1973 | Roob |
| 3,853,122 A | 12/1974 | Bloomberg et al. |
| 3,954,102 A | 5/1976 | Buuck |
| 4,224,934 A | 9/1980 | Scott et al. |
| 4,267,829 A | 5/1981 | Burton et al. |
| 4,335,714 A | 6/1982 | Edgerton et al. |
| 4,342,308 A | 8/1982 | Trick |
| 4,353,360 A | 10/1982 | Finney et al. |
| 4,360,010 A | 11/1982 | Finney |

(Continued)

FOREIGN PATENT DOCUMENTS

| | | |
|---|---|---|
| CA | 2824259 | 3/2014 |
| DE | 3836787 C2 | 5/1990 |

(Continued)

OTHER PUBLICATIONS

American Medical System, AMS 800TM Urinary Control System Operating Room Manual, 2004.

(Continued)

*Primary Examiner* — Samuel Gilbert
(74) *Attorney, Agent, or Firm* — Coloplast Corp., Coloplast A/S; Nick Baumann

(57) ABSTRACT

A pump includes a pump bulb connected to a pump body. An exhaust valve assembly is disposed in the pump body within an exit flow path communicating between the pump bulb and the cylinder. An inlet valve is rotatably disposed in the pump body within an inlet flow path communicating between the reservoir and the pump bulb. The inlet valve includes a spherical part retained in a seat formed by the pump body, an inlet flange connected to and extending radially away from the spherical part, and a lockout flange connected to and extending radially away from the spherical part. A channel is formed through a portion of the spherical part of the inlet valve. The channel includes an outlet hole that is blocked from the inlet flow path by the seat formed in the pump body and opened to the inlet flow path by rotation of the inlet valve.

13 Claims, 11 Drawing Sheets

(56) References Cited

U.S. PATENT DOCUMENTS

| | | |
|---|---|---|
| 4,364,379 A | 12/1982 | Finney |
| 4,383,525 A | 5/1983 | Scott et al. |
| 4,407,278 A | 10/1983 | Burton et al. |
| 4,424,807 A | 1/1984 | Evans et al. |
| 4,441,491 A | 4/1984 | Evans et al. |
| 4,449,520 A | 5/1984 | Palomar et al. |
| 4,545,081 A | 10/1985 | Nestor et al. |
| 4,548,081 A | 10/1985 | Wolthausen |
| 4,559,931 A | 12/1985 | Fischell |
| 4,566,446 A | 1/1986 | Fogarty |
| 4,572,168 A | 2/1986 | Fischell |
| 4,576,234 A | 3/1986 | Upchurch |
| 4,584,994 A | 4/1986 | Bamberger et al. |
| 4,594,997 A | 6/1986 | Hakky |
| 4,596,242 A | 6/1986 | Fischell |
| 4,671,261 A | 6/1987 | Fischell |
| 4,682,583 A | 7/1987 | Burton et al. |
| 4,682,589 A | 7/1987 | Finney |
| 4,816,016 A | 3/1989 | Schulte et al. |
| 4,846,909 A | 7/1989 | Klug et al. |
| 4,982,731 A | 1/1991 | Lue et al. |
| 5,010,882 A | 4/1991 | Polyak et al. |
| 5,062,417 A | 11/1991 | Cowen |
| 5,067,485 A | 11/1991 | Cowen |
| 5,101,813 A | 4/1992 | Trick |
| 5,133,923 A | 7/1992 | Klug |
| 5,141,509 A | 8/1992 | Burton et al. |
| 5,159,920 A | 11/1992 | Condon et al. |
| 5,160,341 A | 11/1992 | Brenneman et al. |
| 5,167,611 A | 12/1992 | Cowan |
| 5,188,596 A | 2/1993 | Condon et al. |
| 5,250,020 A | 10/1993 | Bley |
| 5,254,092 A | 10/1993 | Polyak |
| 5,263,946 A | 11/1993 | Klug |
| 5,454,798 A | 10/1995 | Kubalak et al. |
| 5,558,829 A | 9/1996 | Petrick |
| 5,584,271 A | 12/1996 | Sakata |
| 5,632,777 A | 5/1997 | Petrick |
| 5,653,757 A | 8/1997 | Petrick |
| 5,704,895 A | 1/1998 | Scott et al. |
| 5,725,507 A | 3/1998 | Petrick |
| 5,779,964 A | 7/1998 | Welch et al. |
| 5,851,176 A | 12/1998 | Willard |
| 5,895,424 A | 4/1999 | Steele et al. |
| 5,919,170 A | 7/1999 | Woessner |
| 5,935,362 A | 8/1999 | Petrick |
| 6,039,750 A | 3/2000 | Kubalak et al. |
| 6,060,639 A | 5/2000 | Petrick |
| 6,171,233 B1 | 1/2001 | Willard |
| 6,443,887 B1 | 9/2002 | Derus et al. |
| 6,475,137 B1 | 11/2002 | Elist |
| 6,533,719 B2 | 3/2003 | Kuyava et al. |
| 6,537,192 B1 | 3/2003 | Elliott et al. |
| 6,572,527 B2 | 6/2003 | Steele et al. |
| D476,471 S | 7/2003 | Alfaro |
| 6,599,231 B1 | 7/2003 | Elliott et al. |
| 6,616,593 B1 | 9/2003 | Elliott et al. |
| 6,638,211 B2 | 10/2003 | Suslian et al. |
| 6,639,237 B2 | 10/2003 | Pedersen et al. |
| 6,656,107 B1 | 12/2003 | Pedersen et al. |
| 6,682,471 B2 | 1/2004 | Steele et al. |
| 6,723,042 B2 | 4/2004 | Almli et al. |
| 6,730,017 B2 | 5/2004 | Henkel et al. |
| D496,727 S | 9/2004 | Kubalak et al. |
| D496,993 S | 10/2004 | Kubalak et al. |
| D497,205 S | 10/2004 | Kubalak et al. |
| 6,805,690 B2 | 10/2004 | Ogden et al. |
| 6,808,489 B2 | 10/2004 | George et al. |
| 6,869,390 B2 | 3/2005 | Elliott et al. |
| 6,887,230 B2 | 5/2005 | Kubalak et al. |
| 6,895,998 B2 | 5/2005 | Aoki et al. |
| D508,128 S | 8/2005 | Kubalak et al. |
| 6,935,847 B2 | 8/2005 | Kuyava et al. |
| 6,953,426 B2 | 10/2005 | Barber et al. |
| 6,991,601 B2 | 1/2006 | Kuyava et al. |
| 7,001,307 B2 | 2/2006 | Matsunaga et al. |
| 7,066,878 B2 | 6/2006 | Eid |
| 7,229,400 B2 | 6/2007 | Elliott et al. |
| 7,244,227 B2 | 7/2007 | Morningstar |
| 7,250,026 B2 | 7/2007 | Kuyava |
| 7,350,538 B2 | 4/2008 | Kuyava et al. |
| 7,438,682 B2 | 10/2008 | Henkel et al. |
| 7,494,495 B2 | 2/2009 | Delorme et al. |
| 7,588,598 B2 | 9/2009 | Delorme et al. |
| 7,946,975 B2 | 5/2011 | George et al. |
| 7,996,092 B2 | 8/2011 | Mrva et al. |
| 8,016,746 B2 | 9/2011 | Ellering |
| 8,109,870 B2* | 2/2012 | Kuyava ............... A61F 2/26 600/40 |
| 8,276,591 B2 | 10/2012 | Henkel et al. |
| 8,337,392 B2 | 12/2012 | Morningstar |
| 8,585,580 B2 | 11/2013 | Vaingast et al. |
| 2002/0082473 A1 | 6/2002 | Henkel et al. |
| 2002/0082709 A1 | 6/2002 | Almli et al. |
| 2003/0065249 A1 | 4/2003 | Kuyava et al. |
| 2004/0220447 A1 | 11/2004 | Morningstar |
| 2004/0220448 A1 | 11/2004 | Henkel et al. |
| 2004/0225182 A1* | 11/2004 | Eid ............... A61F 2/26 600/38 |
| 2004/0249397 A1 | 12/2004 | Delorme et al. |
| 2004/0249473 A1 | 12/2004 | Delorme et al. |
| 2005/0010945 A1 | 1/2005 | Hayashi |
| 2005/0027252 A1 | 2/2005 | Boukas |
| 2005/0028418 A1 | 2/2005 | Pargman |
| 2005/0075529 A1 | 4/2005 | Pedersen et al. |
| 2005/0131274 A1 | 6/2005 | Suslian et al. |
| 2005/0209499 A1 | 9/2005 | Elliott et al. |
| 2005/0250981 A1 | 11/2005 | Kuyava et al. |
| 2005/0267320 A1 | 12/2005 | Barber et al. |
| 2005/0278037 A1 | 12/2005 | Delorme et al. |
| 2005/0288692 A1 | 12/2005 | Beraud et al. |
| 2006/0003190 A1 | 1/2006 | Abarra et al. |
| 2006/0012252 A1 | 1/2006 | Miyata et al. |
| 2006/0025753 A1 | 2/2006 | Kubalak et al. |
| 2006/0063960 A1 | 3/2006 | Wissman et al. |
| 2006/0135845 A1 | 6/2006 | Kuyava et al. |
| 2006/0173468 A1 | 8/2006 | Simmon et al. |
| 2006/0224039 A1 | 10/2006 | Steele |
| 2007/0135673 A1 | 6/2007 | Elliott et al. |
| 2007/0142700 A1 | 6/2007 | Fogarty et al. |
| 2011/0118540 A1 | 5/2011 | Morningstar |
| 2012/0022323 A1 | 1/2012 | Forsell |
| 2013/0072751 A1 | 3/2013 | Fogarty |

FOREIGN PATENT DOCUMENTS

| | | |
|---|---|---|
| EP | 0093507 B1 | 11/1983 |
| FR | 2556585 B1 | 6/1985 |
| GB | 1549315 A | 7/1979 |
| WO | 9114409 A1 | 10/1991 |
| WO | 9634581 A1 | 11/1996 |
| WO | 9804214 A1 | 2/1998 |
| WO | 2006066199 A1 | 6/2006 |
| WO | 2007073556 A2 | 6/2007 |
| WO | 2009024024 A1 | 2/2009 |
| WO | 2009094431 A4 | 11/2009 |
| WO | 2012139589 A1 | 10/2012 |

OTHER PUBLICATIONS

International Search Report and Written Opinion issued in PCT/DK2011/050031, mailed Mar. 16, 2011, 5 pages.
International Search Report and Written Opinion issued in PCT/DK2012/000090, mailed Sep. 6, 2013, 16 pages.
Office Action From DK Patent Office Mailed Jun. 23, 2010, 5 pages.

* cited by examiner

Fig. 7A AUTO-LOCK MODE

US 9,554,937 B2

1

PENILE PROSTHETIC PUMP HAVING AN INLET VALVE WITH A LOCKOUT FLANGE

BACKGROUND

An implanted penile prosthetic is a proven approach to relieve erectile dysfunction in men.

A penile prosthetic typically includes two cylinders that are implanted in the corpora cavernosa of the penis, a reservoir implanted in the abdomen that communicates with the cylinder(s), and a pump, often located in the scrotum, that is employed to move liquid from the reservoir into the cylinder(s).

In a typical application, the user squeezes a bulb of the pump multiple times to transfer liquid from the reservoir to the cylinders. Each squeeze of the bulb ejects some liquid to the cylinders. The squeezed (compressed) bulb recovers, creating a suction pressure that draws liquid out of the reservoir and into the bulb. Subsequent squeezing and recovery of the bulb transfers liquid from the reservoir into the cylinders, which inflates the cylinders to provide the user with an erect penis. The user may return the penis to its flaccid state by selectively activating a deflation mechanism and transferring the liquid from the cylinder(s) back into the reservoir.

It is desirable to provide the user with a simple and efficient mechanism for addressing erectile dysfunction.

SUMMARY

One aspect provides a pump that is attachable to a reservoir and a cylinder of an implantable penile prosthetic. The pump includes a pump bulb connected to a pump body. The pump bulb is operable to move liquid from the reservoir to the cylinder. The pump has an exhaust valve assembly disposed in the pump body within an exit flow path communicating between the pump bulb and the cylinder. The pump has an inlet valve rotatably disposed in the pump body within an inlet flow path communicating between the reservoir and the pump bulb. The inlet valve includes a spherical part retained in a seat formed by the pump body, an inlet flange connected to and extending radially away from the spherical part, and a lockout flange connected to and extending radially away from the spherical part. A channel is formed through a portion of the spherical part of the inlet valve. The channel includes an outlet hole that is blocked from the inlet flow path by the seat formed in the pump body and opened to the inlet flow path by rotation of the inlet valve.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

2

Figure 1:
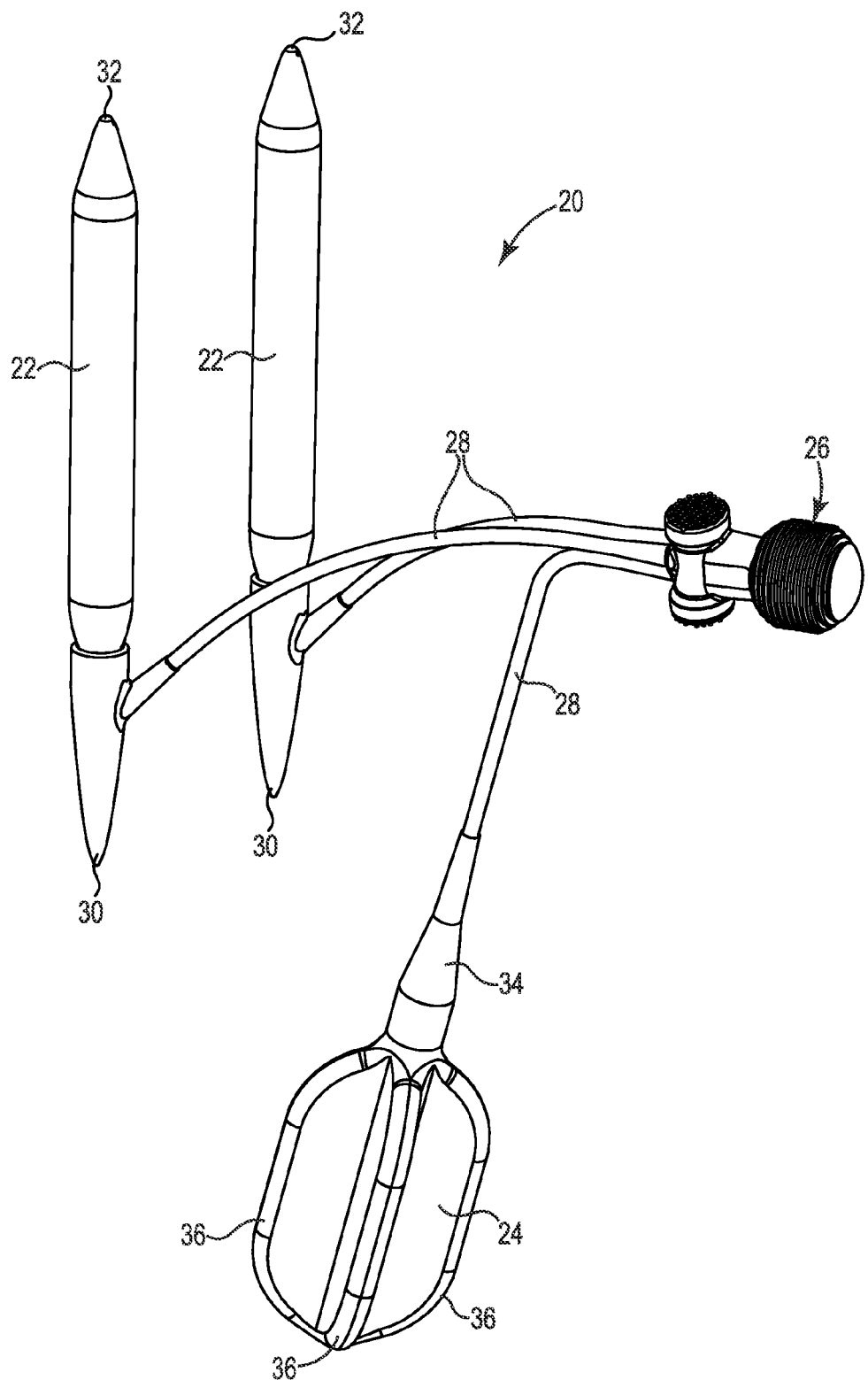
FIG. 1 is a perspective view of one embodiment of a penile prosthetic having a pump that has been connected to a pair of penile cylinders and a reservoir.
Figure 3A:
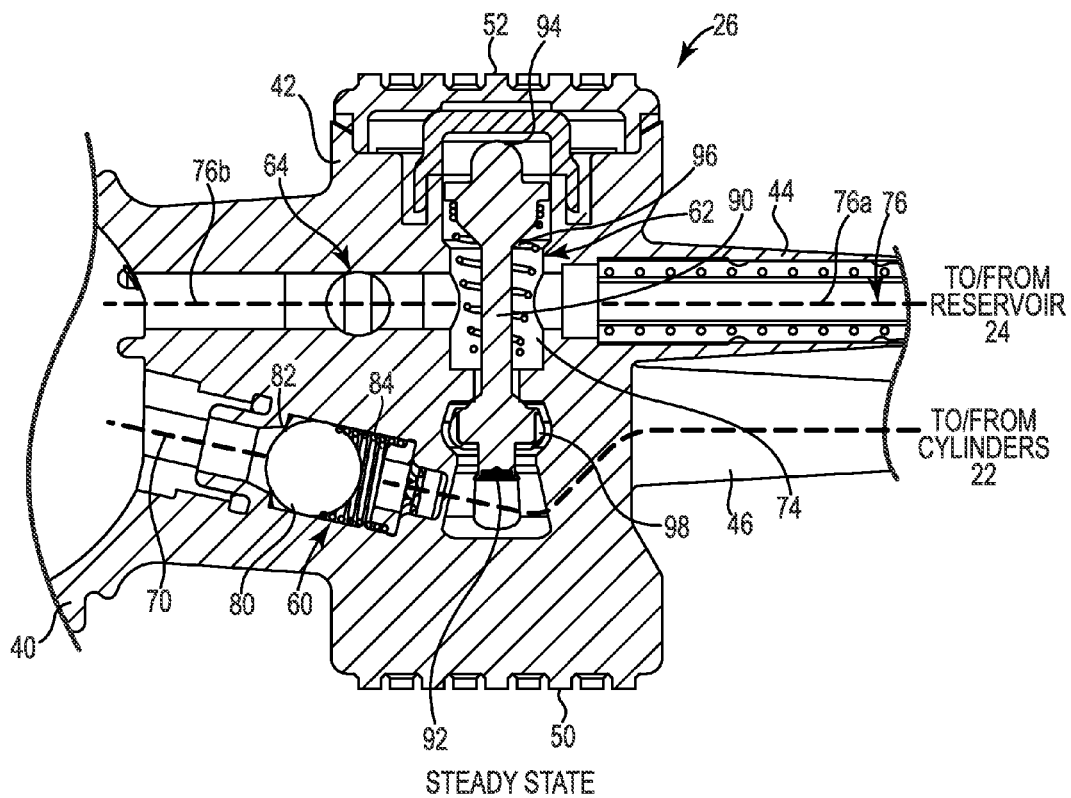

FIG. 3A is a vertical cross-sectional view taken centrally between deflation pads of the pump illustrated in FIG. 1.

Figure 3B:
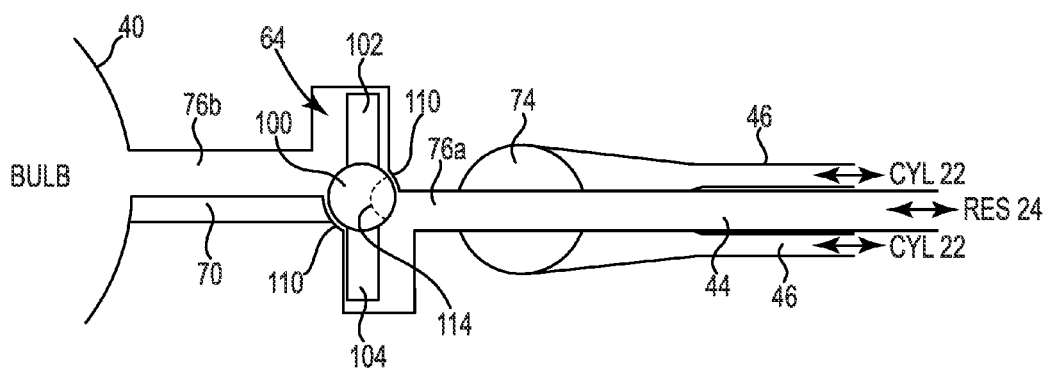

FIG. 3B is a lateral cross-sectional view taken centrally through the pump illustrated in FIG. 1.

Figure 4A:
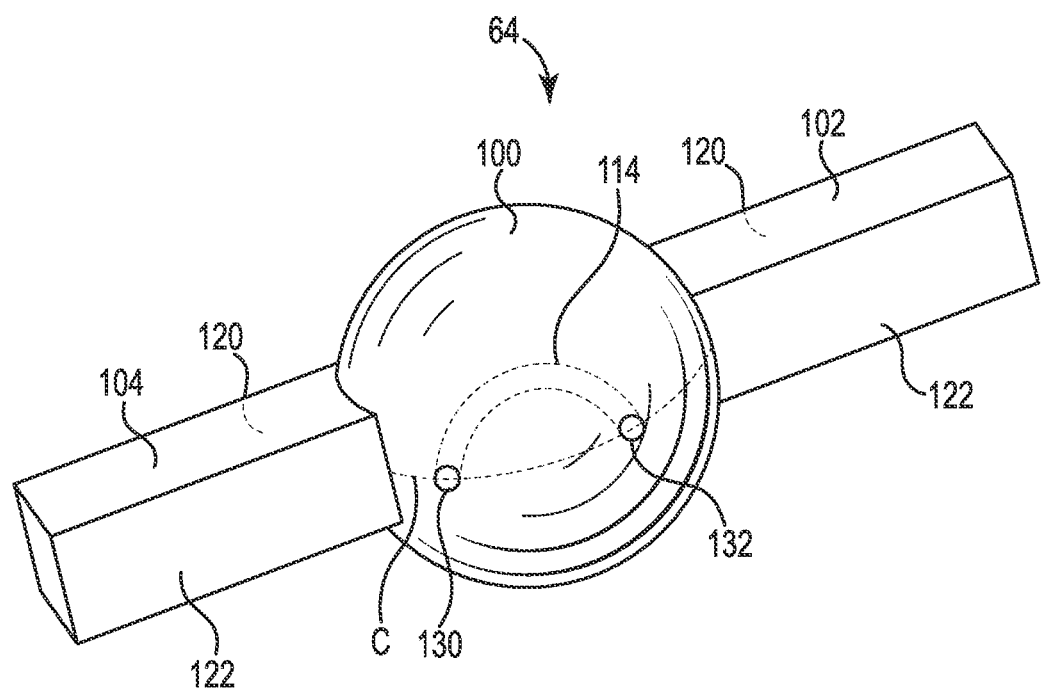
Figure 4B:
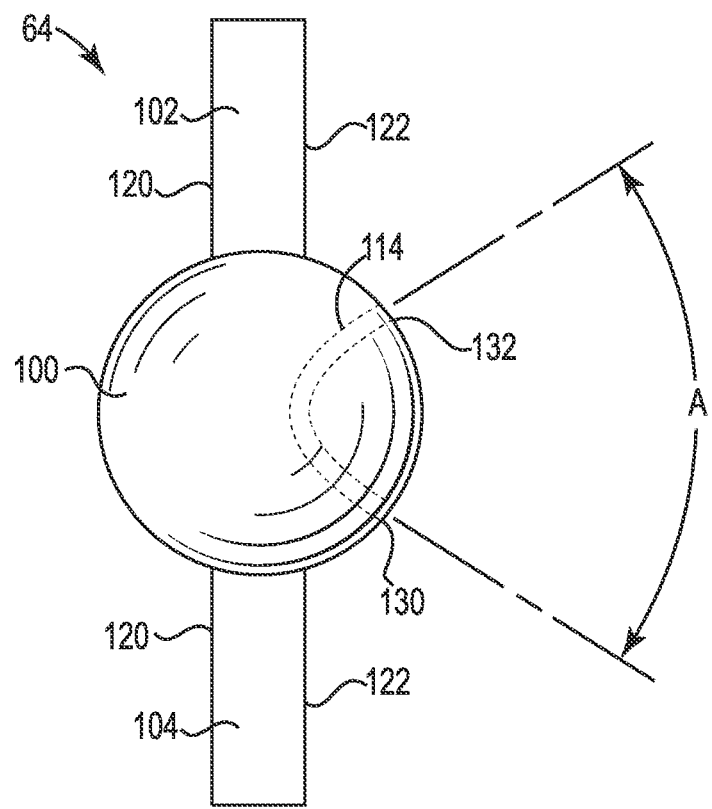
Figure 4C:
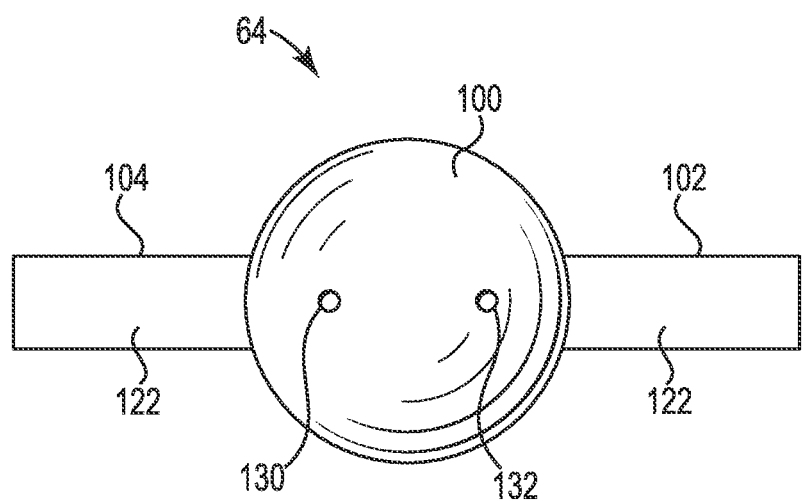

FIG. 4A is a perspective view, FIG. 4B is a top view, and FIG. 4C is a front view of one embodiment of an inlet valve retained within the pump illustrated in FIG. 1.

Figure 5A:
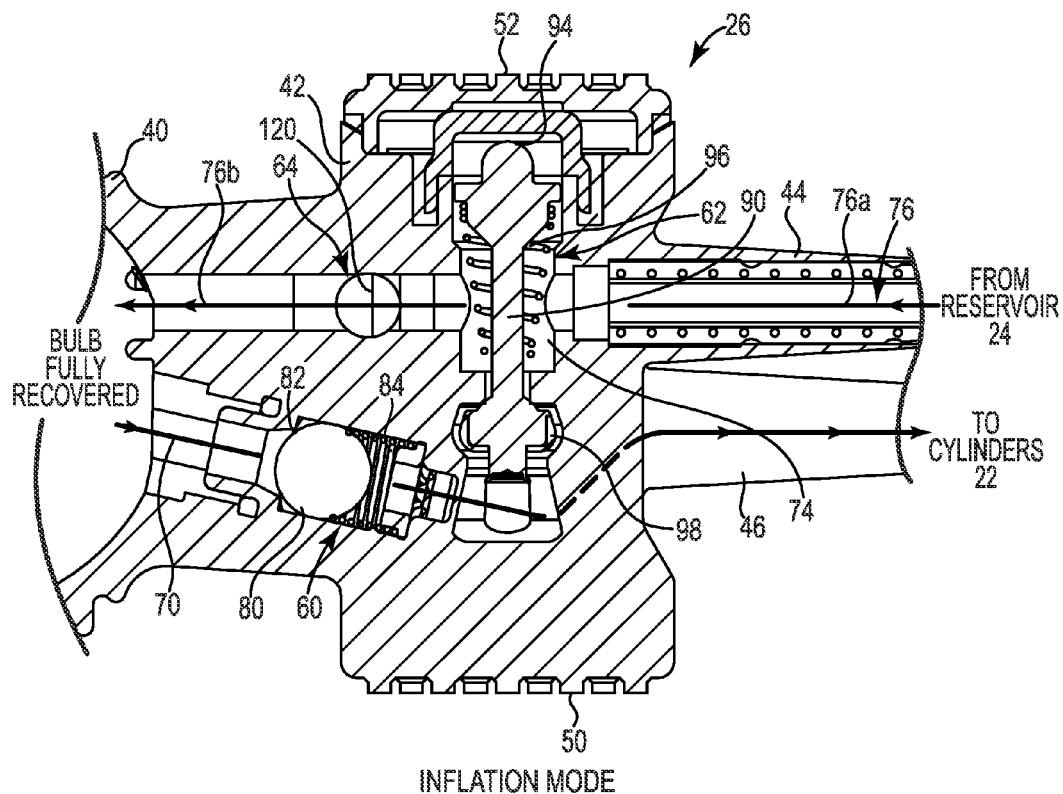

FIG. 5A is a vertical cross-sectional view taken centrally between deflation pads of the pump illustrated in FIG. 1, with the pump in an inflation mode for inflating the cylinders.

Figure 5B:
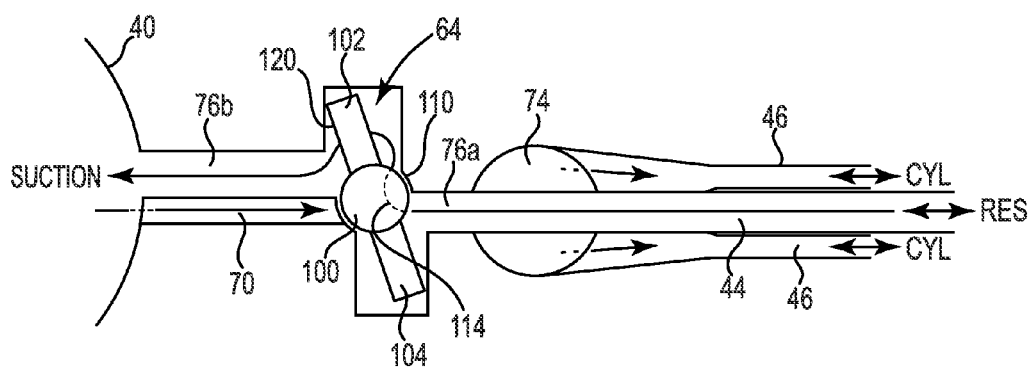

FIG. 5B is a lateral cross-sectional view taken centrally through the pump illustrated in FIG. 1, with the inlet valve rotated in the inflation mode.

Figure 6A:
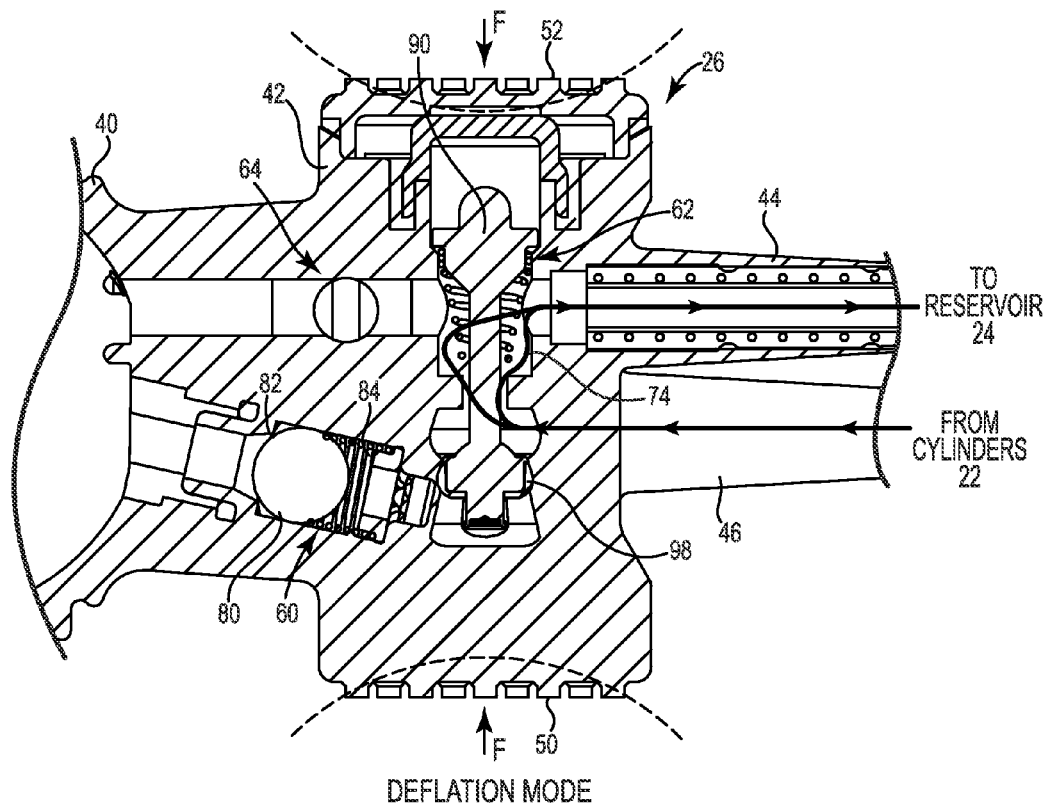

FIG. 6A is a vertical cross-sectional view taken centrally between deflation pads of the pump illustrated in FIG. 1, with the pump in a deflation mode for deflating the cylinders.

Figure 6B:
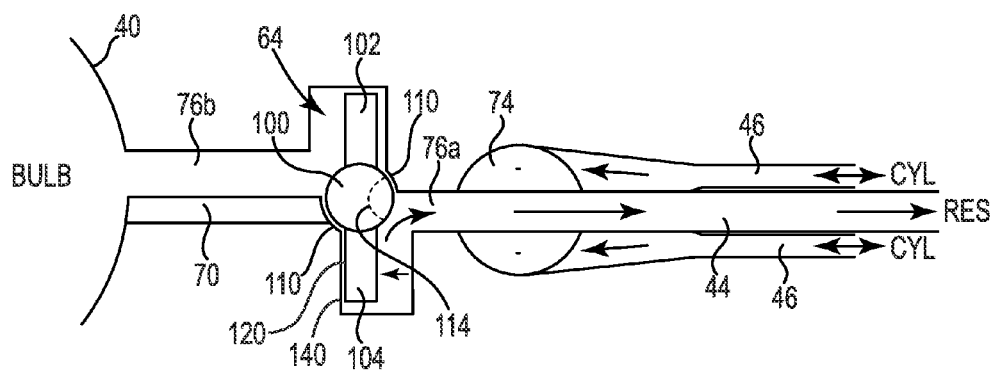

FIG. 6B is a lateral cross-sectional view taken centrally through the pump illustrated in FIG. 1, with the inlet valve rotated closed in the deflation mode.

FIG. 7A is a vertical cross-sectional view taken centrally between deflation pads of the pump illustrated in FIG. 1, with the inlet valve providing the pump with an auto-lock mode.

Figure 7B:
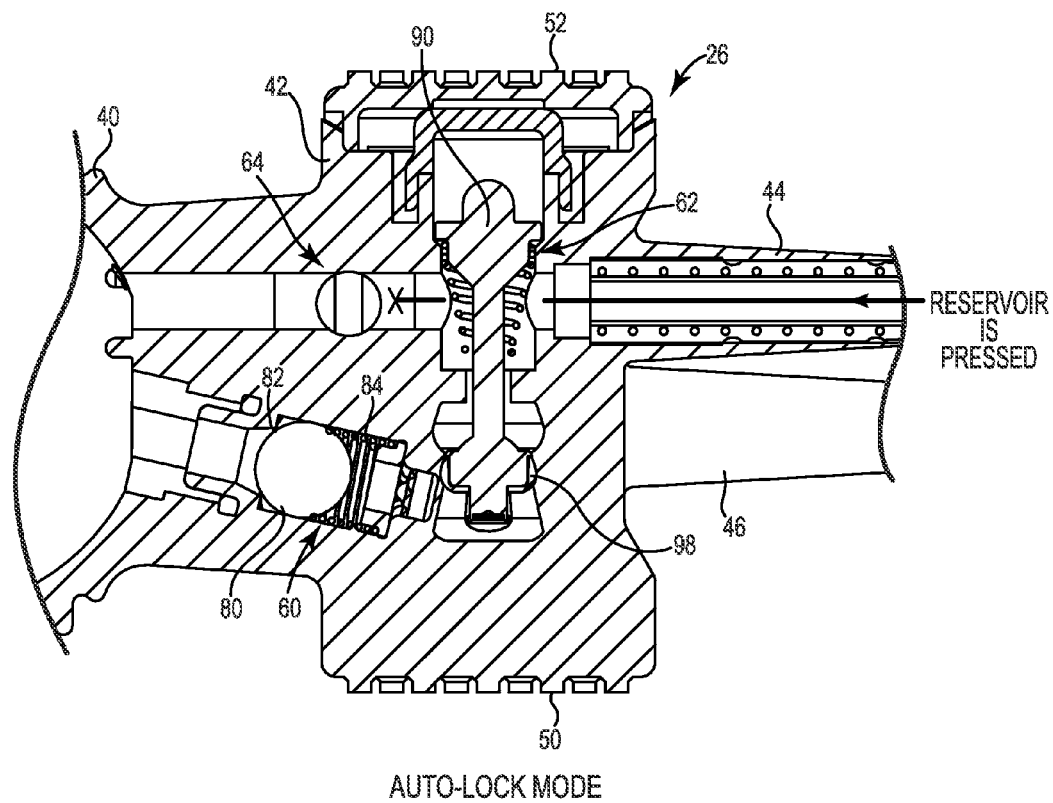
Figure 7B:
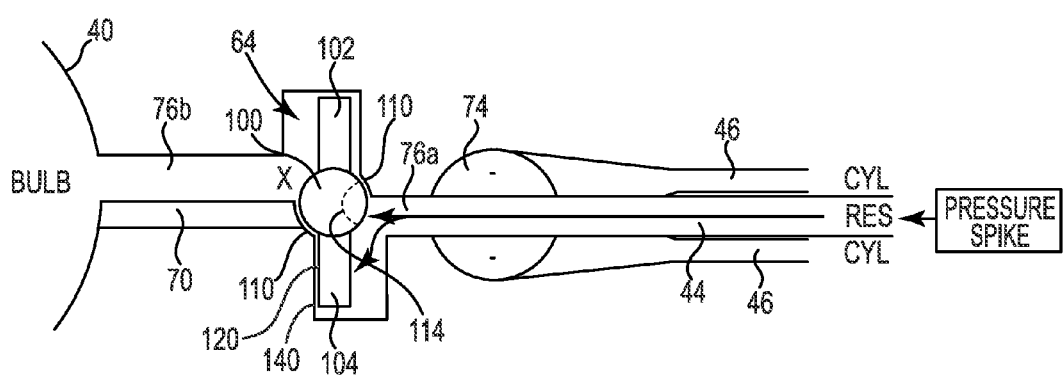

FIG. 7B is a lateral cross-sectional view taken centrally through the pump illustrated in FIG. 1, with the inlet valve in the auto-lock mode to prevent undesirable autoinflation of the cylinders.

Figure 8:
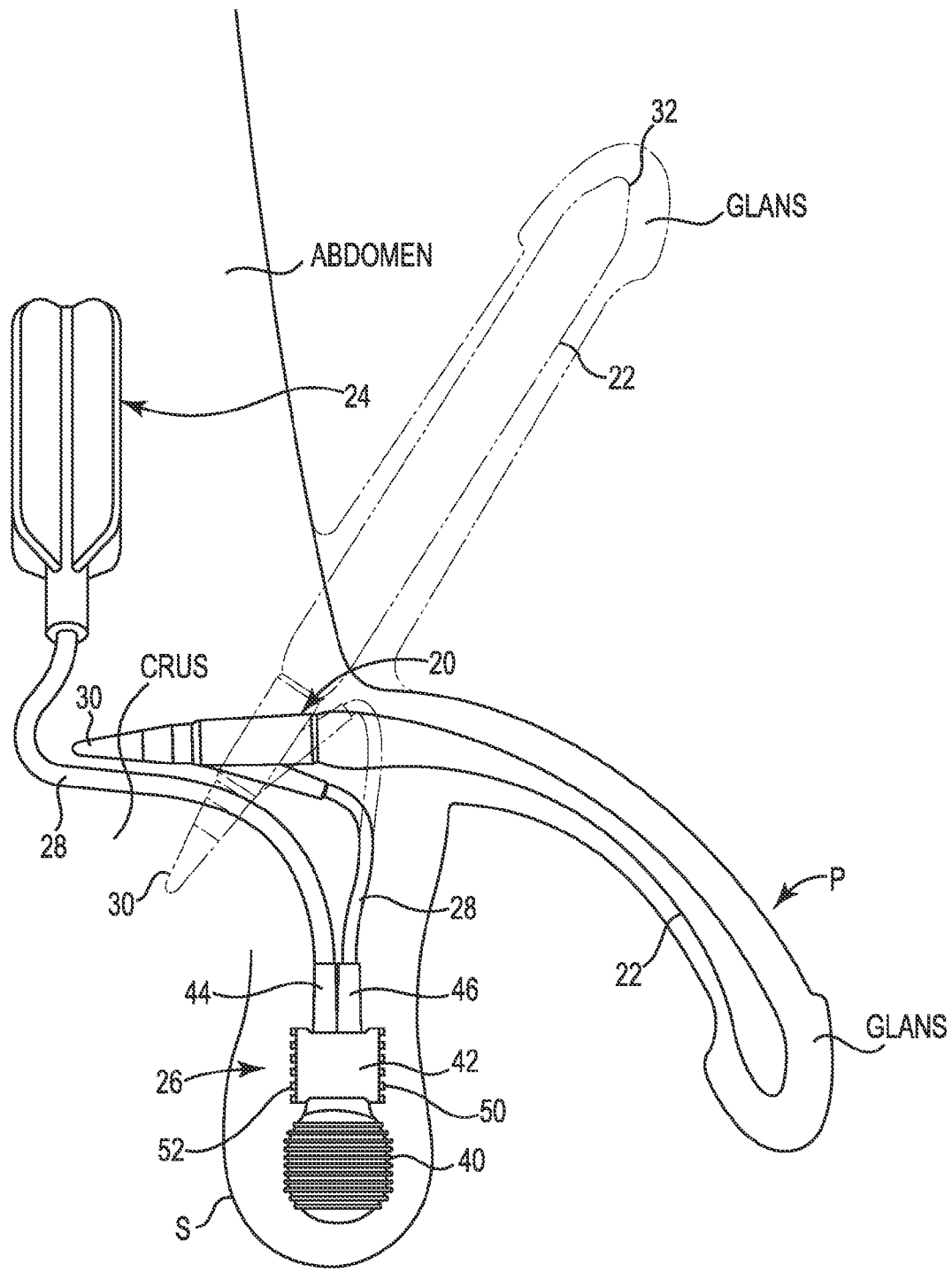

FIG. 8 is a schematic view of one embodiment of the penile prosthetic illustrated in FIG. 1 implanted into a user.

Figure 9A:
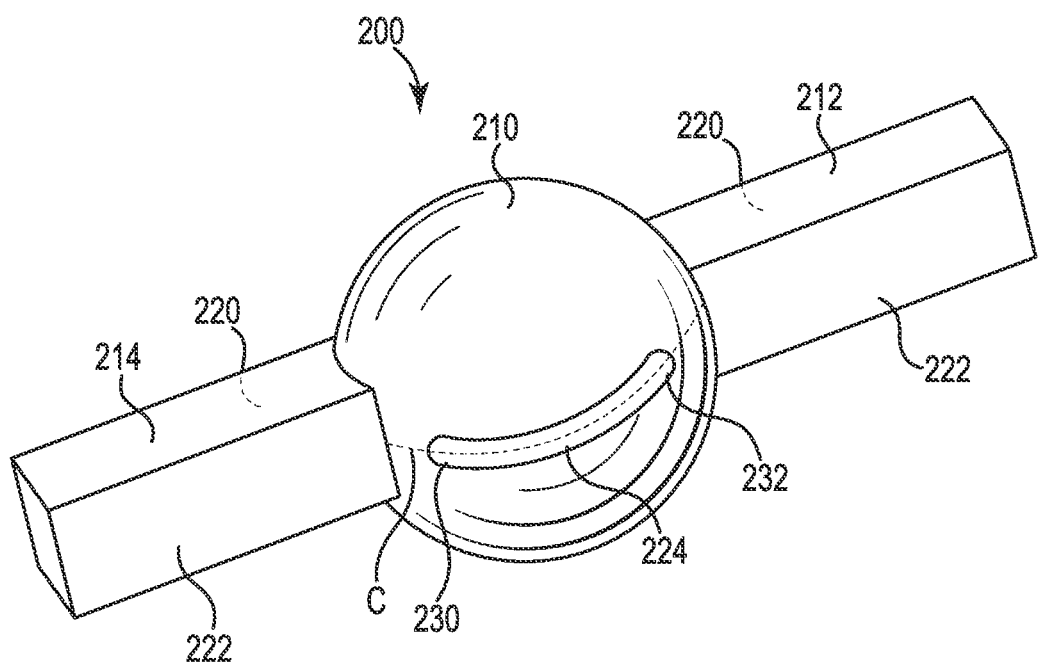
Figure 9B:
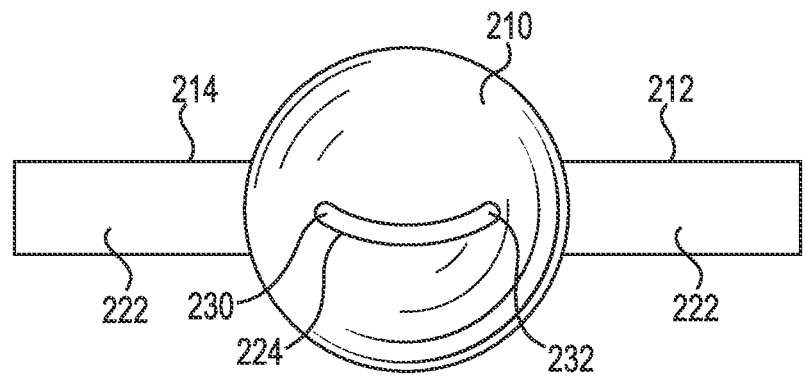
Figure 9C:
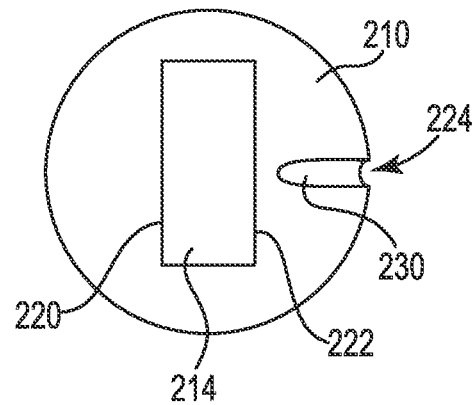

FIG. 9A is perspective view, FIG. 9B is a front view and FIG. 9C is a side view of one embodiment of an inlet valve suitable for use in the pump illustrated in FIG. 1.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

The term "hemisphere" in this application means half of a sphere. One example of a half of a sphere is either the top half or the bottom half on either side of an equator of the sphere. Another example of a half of a sphere is either the left (west) half or the right (east) half on either side of a meridian of the sphere (a longitudinal line extending north-to-south).

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

The term "pressurized" means that a pressure greater than atmospheric pressure is exerted on a fluid. The fluid is said to be pressurized. Atmospheric pressure at sea level is approximately 14 pounds per square inch (PSI).

A penile prosthetic includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir. Pressure spikes delivered unintentionally to the reservoir can result in a stream of pressurized liquid undesirably flowing from the reservoir directly to the cylinders.

Embodiments provide a pump having a rotatable inlet valve with a lockout flange. Contact between a face of the lockout flange and a wall of the pump body prevents high pressure (or pressurized) liquid from flowing from the reservoir to the pump bulb or the cylinders.

Embodiments provide an inlet valve of a pump for a penile prosthetic, where the inlet valve is one monolithically formed part having flanges integrated with a spherical part. The inlet valve has fewer parts than a typical inlet valve assembly, and yet the inlet valve provides all of the functionality of the typical inlet valve assembly plus additional functionality in the form of a lockout feature. The inlet valve described in this specification does more than a typical inlet valve assembly and has at least one fewer parts.

"Autoinflation" means an involuntary inflation of a cylinder implanted in a penis. Autoinflation occurs when the pressure of the liquid in the reservoir is increased sharply, for example by the user leaning against a table and pressurizing the reservoir implanted in the abdomen. The increase in the reservoir pressure can cause the liquid to flow and bypass the pump bulb, resulting in directly inflating the cylinders. The consequence is an unintended and undesirable erection of the penis. In one embodiment, the inlet valve of the pump provides a lockout feature that prevents autoinflation, or pressurized liquid from being forced out of the reservoir directly to the cylinders.

FIG. 1 is a perspective view of one embodiment of a penile prosthetic 20. The penile prosthetic 20 includes cylinders 22 for implantation into a penis, a reservoir 24, and a pump 26 connected to the cylinders 22 and the reservoir 24, for example by kink resistant tubing 28.

Each of the cylinders 22 includes a proximal end 30 opposite a distal end 32. During implantation, the proximal end 30 (also called a rear tip) is implanted toward the crus of the penis and the distal end 32 is implanted within the glans penis. The cylinders 22 are fabricated from material configured to collapse when the cylinders 22 are deflated to provide the penis with a flaccid state and expand when the cylinders 22 are inflated with liquid to provide the penis with an erection. As a point of reference, the cylinders 22 are illustrated in an inflated state. Suitable material for fabricating the cylinders 22 includes silicone, biocompatible polymers such as urethanes, and blends of polymers with urethane, copolymers of urethane, or the like. Suitable cylinders are available from Coloplast Corp., Minneapolis, Minn.

The reservoir 24 is sized to maintain a volume of liquid between about 50-300 ml and includes a neck 34 that is smoothly coupled with the kink resistant tubing 28. In one embodiment, the reservoir 24 is provided as a "cloverleaf" style of reservoir having multiple leafs 36 that may be folded one against the other to compact the reservoir 24 for implantation into the abdomen of the user. One suitable reservoir 24 is sized to retain approximately 130 mL of liquid and is available from Coloplast Corp., Minneapolis, Minn.

Figure 2:
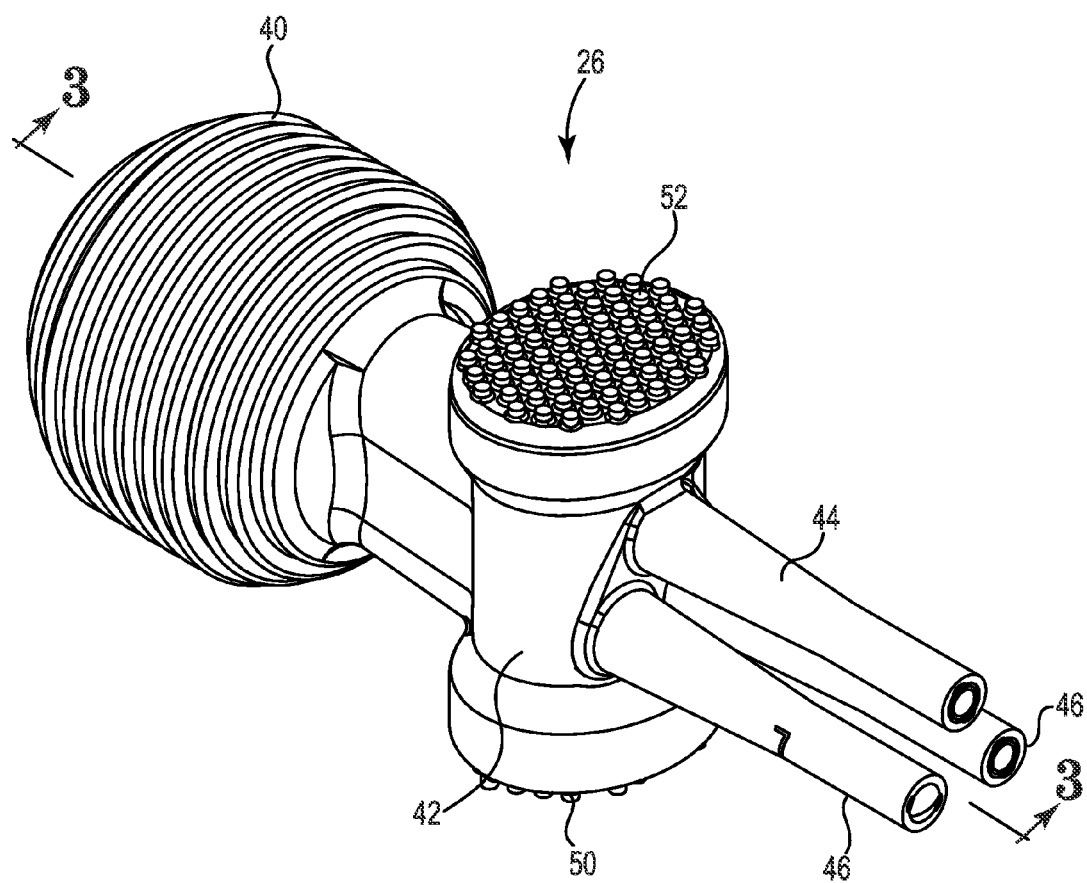
FIG. 2 is a perspective view of the pump illustrated in FIG. 1.

FIG. 2 is a perspective view of the pump 26. The pump 26 includes a pump bulb 40, a pump body 42, an inlet tube 44 connected with the pump body 42, and a pair of exhaust tubes 46 extending from the pump body 42.

In one embodiment, the pump bulb 40 is flexible and includes a ribbed accordion structure that allows the pump bulb 40 to collapse when squeezed to drive liquid out of the pump bulb 40, through the pump body 42, and out of the exhaust tubes 46. The accordion structure allows the pump bulb 40 to recover after being squeezed, which results in an expansion of the bulb 40. Expansion of the pump bulb 40 creates a negative local pressure in the bulb 40 that draws liquid out of the reservoir 24 (FIG. 1), through the inlet tube 44 and the pump body 42, and into the pump bulb 40. Subsequent squeezing of the pump bulb 40 ejects liquid from the pump bulb 40, and draws liquid back into the pump bulb 40 in a cyclical manner.

In one embodiment, the pump body 42 is integrally formed and connected with the pump bulb 40 and includes a first activation surface 50 opposite a second activation surface 52. The activation surfaces 50, 52 (also called deflation pads) are illustrated as non-circular (elliptical) although other shapes for the activation surfaces 50, 52 are also acceptable. The pump body 42 houses or maintains valves (described below) that may be activated/deactivated by pressing the activation surfaces 50, 52.

The inlet tube 44 is connected to the reservoir 24 (FIG. 1) by the kink resistant tubing 28. Each of the exhaust tubes 46 is connected to a respective one of the cylinders 22 via the kink resistant tubing 28. Compressing the pump bulb 40 ejects the liquid from the bulb 40 through the exhaust tubes 46 to the cylinders 22, and expansion of the pump bulb 40 creates suction that draws liquid from the reservoir 24 through the pump body 42 and the inlet tube 44 at a low velocity for delivery into the pump bulb 40.

Generally, the pump 26 is implanted into the scrotum of the user and connected to the cylinders 22 that are implanted into the penis of the user. The reservoir 24 is connected to the cylinders 22 and to the pump 26, and implanted within the abdomen of the user after verification that the connections are leak-free. The pump 26 is fabricated from material suitable for body implantation, such as silicone or the urethane-based materials described above for the cylinders 22 or the reservoir 24.

FIG. 3A is a vertical cross-sectional view taken centrally between the deflation pads 50, 52. The pump 26 includes an exhaust valve assembly 60 located between the pump bulb 40 and the cylinders 22, a deflation valve assembly 62 located between the deflation pads 50, 52, and an inlet valve 64 located between the reservoir 24 and the pump bulb 40. The pump bulb 40 is operable to draw liquid from the reservoir 24.

The exhaust valve assembly 60 is disposed in the pump body 42 within an exit flow path 70 that communicates between the pump bulb 40 and the cylinder 22. Squeezing the pump bulb 40 ejects the liquid through the exhaust valve assembly 60 along the exit flow path 70 and into the cylinders 22 to inflate the cylinders 22 and provide an erection.

The deflation valve assembly 62 is disposed in the pump body 42 in a deflation flow path 74 that is transverse to the exit valve assembly 60 and the inlet valve 64. The deflation valve assembly 62 is displaceable to allow the liquid in the cylinders 22 to drain or flow through the deflation flow path 74 back to the reservoir 24.

The inlet valve 64 is rotatably disposed in the pump body 42 within an inlet flow path 76 that communicates between the reservoir 24 and the pump bulb 40. The inlet flow path 76 is formed in the pump body 42 and has a first portion 76a communicating between the reservoir 24 and the inlet valve 64 and a second portion 76b communicating between the inlet valve 64 and the pump bulb 40. The inlet valve 64 rotates in response to suction on a downstream side to provide a swinging gate that allows liquid to be drawn from the reservoir 24, through the inlet flow path 76, and into the pump bulb 40. The inlet valve 64 also operates to prevent pressurized liquid from being unintentionally forced from the reservoir 24 into the pump bulb 40.

The exhaust valve assembly 60 includes a ball valve 80 that is biased into contact with a surface 82 by a spring 84. The ball valve 80 is configured to be displaced from the surface 82 (thus compressing the spring 84) when liquid flows from the pump bulb 40 through the exhaust valve assembly 60 toward the cylinders 22. For example, compressing the pump bulb 40 ejects liquid from the pump bulb 40, which unseats the ball valve 80 from the surface 82 to allow the liquid to flow past the ball valve 80, along the exit flow path 70, through the deflation valve assembly 62 and into the cylinders 22. The expansion (or recovery) of the pump bulb 40 will create a downstream suction that draws liquid from the reservoir 24, past the inlet valve 64, and into the bulb 40. Subsequent pumping of the bulb 40 ejects the liquid from the bulb 40 into the cylinders 22. The spring 84 biases the ball valve 80 into contact with the surface 82 to block backflow of liquid from the cylinders 22 into the pump bulb 40. In this manner, the exhaust valve assembly 60 is provided as a one-way exhaust valve.

In one embodiment, the pump body 42 is an elastomeric chamber molded around the deflation valve assembly 62. The deflation valve assembly 62 is configured to allow liquid to flow from the reservoir 24 through the inlet flow path 76 and into the pump bulb 40, and out the pump bulb 40 through the exit flow path 70 and into the cylinders 22 during inflation of the cylinders. The deflation valve assembly 62 allows the user to deflate the cylinders 22. For example, in one embodiment pressing on the activation surfaces 50, 52 displaces the deflation valve assembly 62 to block the exit flow path 70, which allows liquid to flow from the cylinders 22 through the deflation flow path 74 in the pump body 42 and back to the reservoir 24, while bypassing the pump bulb 40.

The deflation valve assembly 62 includes a valve stem 90 extending between a first end 92 associated with the deflation pads 50, a second end 94 associated with the deflation pad 52, a spring 96 provided to bias the stem 90 relative to the pump body 42, and a crown 98 movably secured to the stem 90. In one embodiment, the spring 96 is a conical spring with one end of the spring wider than the other. Pushing on the deflation pads 50, 52 displaces the second end 94 of the stem away from the deflation pad 52. During the deflation process, movement of the stem 90 displaces the crown 98 into a lower portion of the deflation flow path 74, which blocks a portion of the exit flow path 70, and opens the deflation flow path 74 for the flow of liquid from the cylinders 22 back to the reservoir 24.

In a subsequent inflation process, squeezing the pump bulb 40 ejects liquid through the exhaust valve assembly 60, which displaces the crown 98 upward to open the exit flow path 74 between the pump bulb 40 and the cylinders 22.

FIG. 3B is a lateral cross-sectional view of the pump 26 looking down on the inlet valve 64. The deflation valve assembly 62 is removed from the illustration of FIG. 3B to improve the viewing clarity, although it is to be understood that the deflation valve assembly 62 is retained within the deflation flow path 74.

In one embodiment, the inlet valve 64 includes a spherical part 100, an inlet flange 102 connected to and extending radially away from the spherical part 100, and a lockout flange 104 connected to and extending radially away from the spherical part 100. In one embodiment, the inlet flange 102 is disposed about 180 degrees apart from the lockout flange 104.

The spherical part 100 is retained in rotational engagement within a seat 110 that is formed by the pump body 42. The spherical part 100 is positioned between the first portion 76a and the second portion 76b of the inlet flow path 76. The spherical part 100 includes a channel 114 that is formed in the spherical part 100. The seat 110 effectively seals the spherical part 100 relative to the pump body 42, and in a closed position, seals the channel 114 from communicating between the first portion 76a and the second portion 76b of the inlet flow path 76.

Rotation of the spherical part 100 (with correlating rotation of the flanges 102, 104) aligns the channel 114 with the first portion 76a and the second portion 76b of the inlet flow path 76. Compression of the pump bulb 40 ejects any liquid in the pump bulb 40 through the exit flow path 70 and into the cylinders 22. The pump bulb 40 subsequently recovers by expanding, which creates a lower suction pressure on the bulb side of the inlet flange 102. The low-pressure on the bulb side of the inlet flange 102 causes the inlet valve 64 to rotate in a counterclockwise manner, which aligns the channel 114 to form a conduit between the first portion 76a and the second portion 76b of the inlet flow path 76. The alignment of the channel 114 within the inlet flow path 76 allows liquid to flow from the reservoir 24, through the spherical part 100, and into the pump bulb 40. The repeated squeezing of the pump bulb 40 thus results in ejection of liquid into the cylinders 22 (when the pump bulb 40 is compressed) and suction of liquid into the pump bulb 40 (when the pump bulb 40 expands and recovers).

FIG. 4A is a perspective view, FIG. 4B is a top view, and FIG. 4C is a front view of the inlet valve 64. The inlet flange 102 and the lockout flange 104 extend radially away from the spherical part 100. As illustrated, the inlet flange 102 is disposed on an opposite side (180 degrees) from the lockout flange 104. Other suitable orientations for the flanges 102, 104 are possible, particularly if accommodated by a complementary change in the pump body 42.

In one embodiment, the channel 114 is formed as a lumen in the spherical part 100. In one embodiment, the channel 114 is formed on a central equator C within a hemisphere of the spherical part 100 between the inlet flange 102 and the lockout flange 104.

With additional reference to FIG. 3B, each of the inlet flange 102 and the lockout flange 104 is provided with a pump bulb face 120 and a reservoir face 122. When assembled into the pump body 42, the pump bulb face 120 is located closer to the pump bulb 40 than to the reservoir 24, and the reservoir face 122 is located closer to the reservoir 24 than to the pump bulb 40. In one embodiment, a height of the inlet flange 102 is the same as a height of the lockout flange 104, and each of the flanges 102, 104 has a height that is less than a diameter of the spherical part 100.

In one embodiment, the channel 114 is formed as a lumen in the spherical part 100 that extends between an entrance hole 130 and an outlet hole 132. The entrance hole 130 is connected to the outlet hole 132, and both are formed in a hemisphere of the spherical part 100 between the reservoir face 122 of the inlet flange 102 and the reservoir face 122 of the lockout flange 104. In one embodiment, the entrance hole 130 is separated from the outlet hole 132 by an angle A that measures in a range from 45-75 degrees. One suitable angle A measured between the entrance hole 130 and the outlet hole 132 is approximately 60 degrees.

The inlet valve 64 is suitably fabricated from metal or plastic. One suitable metal is stainless steel. Suitable plastics include acrylonitrile-butadiene-styrene, polyvinylchloride, or polypropylene to name several.

FIG. 5A is a vertical cross-sectional view taken centrally between deflation pads 50, 52 of the pump 26 and FIG. 5B is a lateral cross-sectional view taken centrally through the pump 26. The view illustrated in FIG. 5B is looking down on the deflation flow path 74 (the inlet valve 64 is not shown), which locates the exhaust valve assembly 60 under (and hidden from view by) the inlet valve 64. The pump 26 is in an inflation mode after the pump bulb 40 has fully recovered.

The recovery of the pump bulb 40 creates suction inside the pump bulb 40 and in the second portion 76b of the inlet flow path 76. The suction in the downstream inlet flow path 76 creates a local low-pressure on the pump bulb face 120 of the inlet flange 102, which causes the inlet flange 102 and the spherical part 100 to rotate in a counterclockwise direction. The rotation of the spherical part 100 aligns the channel 114 with the first portion 76a and with the second portion 76b of the inlet flow path 76. In this manner, the inlet flow path 76 is open to allow liquid flow between the reservoir 24 and the pump bulb 40. Subsequent squeezing or compression of the pump bulb 40 ejects the liquid in the pump bulb 40 through the exit flow path 70 and into the cylinders 22.

FIG. 6A is a vertical cross-sectional view taken centrally between deflation pads 50, 52 of the pump 26 and FIG. 6B is a lateral cross-sectional view taken centrally through the pump 26. The view illustrated in FIG. 6B is looking down on the deflation flow path 74 (the inlet valve 64 is not shown), which locates the exhaust valve assembly 60 under (and hidden from view by) the inlet valve 64. The pump 26 is in the deflation mode.

The user is instructed to touch the deflation pads 50, 52 and apply a force that displaces the stem 90 of the deflation valve assembly 62 downward. Movement of the stem 90 downward results in the crown 98 being displaced downward to close the exit flow path 70 and to open the deflation flow path 74 between the cylinders 22 and a reservoir 24. The ball valve 80 is forced onto the seat 82 by the pressure of the liquid in the deflation flow path 74.

In addition, the pressure of the liquid in the deflation flow path 74 pushes on the lockout flange 104 to press the pump bulb face 120 of the inlet valve 64 against a wall 140 associated with the inlet flow path 76. The contact between the pump bulb face 120 of the lockout flange 104 and the wall 140 prevents the pressurized liquid in the deflation flow path 74 from undesirably flowing into the pump bulb 40. The channel 114 formed in the inlet valve 64 is closed off by the seat 110 that is formed by the pump body 42. In this manner, the lockout flange 104 of the inlet valve 64 provides a lockout feature that prevents the undesired flow of liquid into the pump bulb 40 during deflation of the pump 26.

As described with respect to FIGS. 5A-6B above, the spherical part 100 rotates between a closed position in which the outlet hole 132 is blocked from the second portion 76b of the inlet flow path by the pump body 42, and an opened position in which the channel 114 forms a conduit connecting between the first portion 76a and the second portion 76b of the inlet flow path 76.

FIG. 7A is a vertical cross-sectional view taken centrally between deflation pads 50, 52 of the pump 26 and FIG. 7B is a lateral cross-sectional view taken centrally through the pump 26. The view illustrated in FIG. 7B is looking down on the deflation flow path 74 (the inlet valve 64 is not shown), which locates the exhaust valve assembly 60 under (and hidden from view by) the inlet valve 64. The pump 26 is at steady state with the inlet valve 64 providing an auto-lock mode that prevents unintended pressure spikes applied to the reservoir 24 from delivering a flow of liquid into the cylinders 22.

When the penile prosthetic system 20 is implanted into the user, the cylinders 22 are located in the penis, the reservoir 24 is typically implanted in the abdomen, and the pump 26 is implanted in the scrotum. In the steady state, the liquid is retained in the reservoir 24 and the cylinders 22 are flaccid. Strenuous physical activity or outside pressure applied to the abdomen has the potential to create a pressure spike in the reservoir 24, which could undesirably cause liquid to flow from the reservoir 24, through the pump bulb 40, and into the cylinders 22. The undesirable inflation of the cylinders 22 that arises from a large pressure applied to the reservoir 24 is referred to as autoinflation.

In one embodiment, the inlet valve 64 provides a lockout feature to prevent autoinflation of the cylinders 22. An unexpected pressure spike applied to the reservoir 24 will pressurize the liquid on the reservoir side of the inlet valve 64. The pressurized liquid applies a force against the lockout flange 104. The increased pressure applied on the reservoir face 122 of the inlet valve 64 forces the pump bulb face 120 of the valve 64 against the wall 140 to create and maintain a seal between the inlet valve 64 and the inlet flow path 76. A seal is created between the pump bulb face 120 and wall 140, and between the spherical part 100 and the seat 110. Consequently, the pressurized liquid on the reservoir side of the inlet valve 64 is unable to flow to the second portion 76b of the inlet flow path 76 and is prevented from entering the pump bulb 40. In this manner, the inlet valve 64 provides an auto-lock mode for the pump 26.

FIG. 8 is a schematic side view of the penile prosthetic 20 implanted in a user. The cylinders 22 are implanted in the penis P with the proximal end 30 inserted near the crus and the distal end 32 implanted within the glans. The reservoir 24 is implanted within the abdomen and the pump 26 is implanted within the scrotum S. The penile prosthetic 20 is operable consistent with the description above to inflate the cylinders 22 such that the penis P achieves an erect state (as described in FIGS. 5A and 5B above). The deflation valve assembly 62 (FIG. 3A) operates as described in FIGS. 6A and 6B above to drain liquid out of the cylinders 22 and return the penis P to a flaccid state.

In one embodiment, the pump 26 provides a one-touch release mechanism that allows the cylinders 22 to easily and quickly deflate by an initial, nearly instantaneous activation of the surfaces 50, 52 as opposed to the user applying prolonged pressure (e.g., more than three seconds of applied pressure) to the surfaces 50, 52. Thus, a quick and convenient approach is provided for the rapid deflation of the inflated cylinders 22, which is appreciated by users with limited dexterity.

Referring to FIGS. 5A-5B and FIG. 8, one embodiment of the inlet valve 64, the exhaust valve assembly 60, and the deflation valve assembly 62 has this sequence of inflation operations: The Penis P is flaccid and reservoir 24 is filled with liquid. The inlet valve 64 is closed, the exhaust valve assembly 60 is closed, and the deflation valve assembly 62 is open (if the penis had been previously made erect). The pump bulb 40 is squeezed and the exhaust valve assembly 60 opens as the ball valve 80 compresses the spring 84 to allow the liquid to leave the pump bulb 40 and flow to the cylinders 22. Liquid flowing toward the cylinders 22 will push the crown 98 upward to close the deflation valve assembly 62, thus opening the exit flow path 70 to the cylinders 22. The deflation valve assembly 62 is closed and remains closed during subsequent pumping of the pump bulb 40 that drives liquid out of the pump bulb 40 through the exhaust valve assembly 60 to the penile cylinders 22. When the pump bulb 40 is released during pumping action, the bulb volume expands to create suction. The suction in the pump bulb 40 creates a local low pressure on the pump bulb face 120 of the inlet valve 64, which causes the inlet valve 64 to open. Liquid is drawn from the reservoir 24 through the inlet valve 64 to the pump bulb 40. The exhaust valve assembly 60 is closed when the pump bulb 40 is released during pumping action, and remains closed until the bulb 40 is squeezed. The deflation valve assembly 62 remains closed during the inflation of the cylinders 22. Squeezing the bulb 40 ejects the liquid from the bulb 40 and through the exhaust valve assembly 60.

Referring to FIGS. 6A-6B and FIG. 8, one embodiment of the exhaust valve assembly 60, and the deflation valve assembly 62 has this sequence of deflation operations: The penis P is erect and the cylinder(s) 22 are filled. The inlet valve 64 is closed, the exhaust valve assembly 60 is closed, and the deflation valve assembly 62 is closed. The surfaces 50, 52 are pushed to open the deflation valve assembly 62, and the liquid flows from the penile cylinder(s) 22 transversely through the deflation valve assembly 62 along the deflation flow path 74 in the pump body 42 to the reservoir 24. The liquid in the cylinders 22 drains out of the cylinders 22 and to the reservoir 24. The inlet valve 64 is closed and the exhaust valve assembly 60 is closed.

Referring to FIGS. 7A-7B and FIG. 8, one embodiment of the inlet valve 64, the exhaust valve assembly 60, and the deflation valve assembly 62 has this sequence of anti-autoinflation operations: The penis P is flaccid and the reservoir 24 is filled with liquid. The inlet valve 64 is closed, the exhaust valve assembly 60 is closed, and the deflation valve assembly 62 is closed. The reservoir 24 is pressurized, either through a natural body function (e.g., sneezing) or through an external force (e.g., strenuous exercise or the user pressing against a table edge). The pressurized liquid in the reservoir 24 applies a force against the reservoir face 122 of the lockout flange 104. The increased pressure applied on the reservoir face 122 of the inlet valve 64 forces the pump bulb face 120 of the valve 64 against the wall 140 to create and maintain a seal between the inlet valve 64 and the inlet flow path 76. Consequently, the pressurized liquid on the reservoir side of the inlet valve 64 is unable to flow into the second portion 76b of the inlet flow path 76 and is prevented from entering the pump bulb 40.

FIG. 9A is perspective view, FIG. 9B is a front view and FIG. 9C is a side view of one embodiment of an inlet valve 200 suitable for use in the pump 26 illustrated in FIG. 1.

The inlet valve 200 includes a spherical part 210, an inlet flange 212 connected to and extending radially away from the spherical part 210, and a lockout flange 214 connected to and extending radially away from the spherical part 210. As illustrated, the inlet flange 212 is disposed on an opposite side (180 degrees) from the lockout flange 214. Other suitable orientations for the flanges 212, 214 are possible, particularly if accommodated by a complementary change in the pump body 42.

Each of the inlet flange 212 and the lockout flange 214 has a pump bulb face 220 and a reservoir face 222. When assembled into the pump 26, the pump bulb face 220 is located closer to the pump bulb 40 than to the reservoir 24, and the reservoir face 222 is located closer to the reservoir 24 than to the pump bulb 40. In one embodiment, a height of the inlet flange 202 is the same as a height of the lockout flange 204, and each of the flanges 212, 214 has a height that is less than a diameter of the spherical part 210.

The inlet valve 200 is provided with a channel 224 that functions in a manner similar to the channel 114 described above in FIGS. 4A-4C. In one embodiment, the channel 224 is a groove that is formed in an exterior surface of the spherical part 210 so that the channel is exposed on the exterior surface. The channel 224 (or groove 224) is formed in the spherical part 210 along a central equator C on the reservoir face side of the valve 200. The groove 224 extends from an entrance 230 to an exit 232 for about 60 degrees along the equator C of the spherical part 210, or between the 2 o'clock position and the 4 o'clock position when viewed from above.

One suitable shape of the groove 224 is a semi-circular cut made in the exterior surface of the spherical part 210, for example by a ball-end mill to provide the groove 224 a convex curvature along the exterior surface of the spherical part 210 and with a concave curvature in longitudinal cross-section.

With reference to FIG. 5B, the inlet valve 200 is integrated into the pump 26 between the suction bulb 40 and the reservoir 24. Suction created by the pump bulb 40 creates a lower pressure area on the pump bulb face 220 of the inlet valve 200, which causes the inlet valve 200 to rotate in a counterclockwise manner to align the entrance 230 with the first portion 76a of the inlet flow path 76 communicating with the reservoir 24 and to align the exit 232 with the second portion 76b of the inlet flow path 76 communicating with the pump bulb 40. In this manner, the flow path is open between the reservoir 24 and the pump bulb 40.

The inlet valve 200 is suitably fabricated from metal or plastic. One suitable metal is stainless steel. Suitable plastics include acrylonitrile-butadiene-styrene, polyvinylchloride, or polypropylene to name several.

Embodiments provide a pump for penile prosthetic that has fewer moving parts. The inlet bills described above are formed as an integrated monolithic piece that rotates to open the flow path between the reservoir and the pump bulb, and moves to close the flow path to provide a lockout feature that prevents unintended autoinflation of the cylinders.

Although specific embodiments have been illustrated and described in this disclosure, it will be appreciated by those of ordinary skill in the art that a variety of alternate and/or equivalent implementations may be substituted for the specific embodiments shown and described without departing from the scope of this disclosure. This application is intended to cover any adaptations or variations of the above-disclosed medical devices. Therefore, it is intended that this invention is limited only by the claims and their equivalents.

What is claimed is:

1. A pump adapted for use with an implantable penile prosthetic, the pump comprising:
    a pump bulb connected to a pump body, where the pump is attachable during implantation to a reservoir and to an inflatable cylinder, and the pump bulb is operable to move liquid from the reservoir to the inflatable cylinder;
    an exhaust valve assembly disposed in the pump body within an exit flow path communicating between the pump bulb and the inflatable cylinder;
    an inlet valve rotatably disposed in the pump body within an inlet flow path communicating between the reservoir and the pump bulb, the inlet valve includes a spherical part retained in a seat formed by the pump body, an inlet flange connected to and extending radially away from the spherical part, and a lockout flange connected to and extending radially away from the spherical part; and
    a channel formed through a portion of the spherical part of the inlet valve, with the channel including an outlet hole that is blocked from the inlet flow path by the seat formed in the pump body and opened to the inlet flow path by rotation of the inlet valve.

2. The pump of claim 1, wherein the channel is a lumen formed in the spherical part of the inlet valve.

3. The pump of claim 1, wherein the channel is a groove formed in an exterior surface of the spherical part of the inlet valve.

4. The pump of claim 1, wherein each of the inlet flange and the lockout flange has a pump bulb face that is located closer to the pump bulb than to the reservoir and a reservoir face that is located closer to the reservoir than to the pump bulb, and the inlet valve is configured such that contact between the pump bulb face of the lockout flange and a wall of the inlet flow path prevents pressurized liquid from flowing from the reservoir to the pump bulb.

5. The pump of claim 4, wherein the channel is a lumen extending between an entrance hole and the outlet hole, with both of the entrance hole and the outlet hole formed in the spherical part of the inlet valve between the reservoir face of the inlet flange and the reservoir face of the lockout flange.

6. The pump of claim 4, wherein the channel is a groove formed in an exterior surface of the spherical part of the inlet valve between the reservoir face of the inlet flange and the reservoir face of the lockout flange.

7. The pump of claim 1, wherein the inlet flange is disposed 180 degrees apart from the lockout flange.

8. The pump of claim 1, wherein the channel has an entrance hole in communication with the outlet hole, with the entrance hole separated from the outlet hole by an angle that measures in a range from 45-75 degrees.

9. The pump of claim 1, wherein the channel has an entrance hole in communication with the outlet hole, with the entrance hole separated from the outlet hole by an angle of 60 degrees.

10. The pump of claim 1, further comprising:
    a deflation valve assembly disposed in the pump body transverse to the exhaust valve assembly and the inlet valve.

11. The pump of claim 10, wherein the deflation valve assembly has a stem that is movable relative to the pump body and a crown that is separate from and movable relative to the stem.

12. The pump of claim 11, wherein the inlet valve is rotatably disposed in the pump body between the deflation valve assembly and the pump bulb.

13. The pump of claim 1, further comprising:
    a deflation valve assembly disposed in the pump body and positioned between the inlet valve and the reservoir.

* * * * *